United States Patent
Stack et al.

(10) Patent No.: US 6,803,368 B2
(45) Date of Patent: Oct. 12, 2004

(54) ANTIPSYCHOTIC AMINOMETHYL DERIVATIVES OF 7,8-DIHYDRO-3H-6,9-DIOXA-1,3-DIAZA-CYCLOPENTA[A]NAPHTHALENE

(75) Inventors: Gary P. Stack, Ambler, PA (US); James A. Nelson, Washington Crossing, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/128,058

(22) Filed: Apr. 23, 2002

(65) Prior Publication Data

US 2002/0183330 A1 Dec. 5, 2002

Related U.S. Application Data

(60) Provisional application No. 60/286,229, filed on Apr. 25, 2001.

(51) Int. Cl.⁷ .................... C07D 491/04; C07D 519/00; A61K 31/4188; A61P 25/00
(52) U.S. Cl. ............... 514/252.14; 514/252.15; 514/252.19; 514/254.06; 514/256; 514/277; 514/278; 514/318; 514/319; 514/322; 514/394; 544/295; 544/357; 544/370; 546/19; 546/199; 546/273.1; 548/300.4; 548/300.7; 548/302.1
(58) Field of Search ................. 544/295, 357, 544/370; 546/19, 194, 273.1, 199; 548/300.7, 300.4, 302.1; 514/252.14, 252.15, 252.19, 254.06, 256, 277, 278, 318, 319, 322, 394

(56) References Cited

U.S. PATENT DOCUMENTS

| | | | |
|---|---|---|---|
| 5,318,988 A | 6/1994 | Schohe-Loop et al. | 514/458 |
| 5,371,094 A | 12/1994 | Heine et al. | 514/323 |
| 5,756,532 A | 5/1998 | Stack et al. | 514/411 |
| 5,869,490 A | 2/1999 | Stack | 514/225 |

FOREIGN PATENT DOCUMENTS

| | | |
|---|---|---|
| WO | WO 91/13872 | 9/1991 |
| WO | WO 97/23485 | 7/1997 |
| WO | WO 98/29415 | 7/1998 |
| WO | WO 98/40386 | 9/1998 |

*Primary Examiner*—Bruck Kifle
(74) *Attorney, Agent, or Firm*—Woodcock Washburn LLP

(57) ABSTRACT

Compounds of the formula

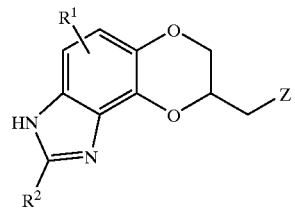

useful for treatment of disorders of the dopaminergic system, such as schizophrenia, schizoaffective disorder, bipolar disorder, Parkinson's disease, L-DOPA induced pychoses and dyskinesias, Tourette's syndrome and hyperprolactinemia and in the treatment of drug addiction such as the addiction to ethanol, nicotine or cocaine and related illnesses.

38 Claims, No Drawings

ANTIPSYCHOTIC AMINOMETHYL DERIVATIVES OF 7,8-DIHYDRO-3H-6,9-DIOXA-1,3-DIAZA-CYCLOPENTA[A]NAPHTHALENE

BACKGROUND OF THE INVENTION

The application claims priority from co-pending provisional application serial No. 60/286,229, filed on Apr. 25, 2001, the entire disclosure of which is hereby incorporated by reference.

The clinical treatment of schizophrenia has long been defined by the dopamine hypothesis of schizophrenia, which holds that schizophrenia is a result of hyperactivity of dopaminergic neurotransmission, particularly in limbic brain structures such as nucleus accumbens (the mesolimbic dopamine system). Indeed, the positive symptoms of schizophrenia (hallucinations, delusions, thought disorder) are successfully treated with neuroleptics, which block dopamine receptors. However, such treatment is accompanied by the production of movement disorders or dyskinesias (extrapyramidal side effects), due to the blockade of nigrostriatal dopamine receptors. In addition, neuroleptics do not treat the negative symptoms of schizophrenia (social withdrawal, anhedonia, poverty of speech) which are related to a relative hypoactivity of neurotransmission in the mesocortical dopamine system and which respond to treatment by dopamine agonists.

Efforts to induce antipsychotic activity with dopamine autoreceptor agonists have been successful (Corsini et al., Adv. Biochem. Psychopharmacol. 16, 645–648, 1977; Tamminga et al., Psychiatry 398–402, 1986). Dopamine autoreceptor agonists produce a functional antagonism of dopaminergic neurotransmission by the reduction of neuronal firing and the inhibition of dopamine synthesis and release. Since dopamine autoreceptor agonists are partial agonists at postsynaptic dopamine receptors, they provide a residual level of stimulation sufficient to prevent the production of dyskinesias. Indeed, partial agonists are capable of functioning as either agonists or antagonists depending on the level of dopaminergic stimulation in a given tissue or brain region, and would therefore be expected to have efficacy versus both positive and negative symptoms of schizophrenia. Thus, novel dopamine partial agonists are of great interest for the treatment of schizophrenia and related disorders.

DESCRIPTION OF THE INVENTION

In accordance with this invention, there is provided a group of novel compounds of the formula:

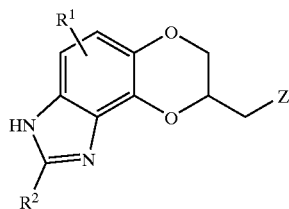

I wherein
$R^1$ and $R^2$ are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

Z is $NR^3$—$(CH_2)_n$—Y,

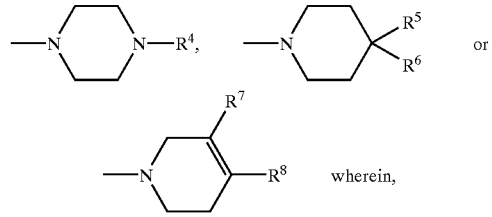

wherein,

Y is hydrogen, hydroxy, cycloalkyl of 3 to 15 carbon atoms, or phenyl, substituted phenyl, phenoxy, substituted phenoxy, naphthyl, substituted naphthyl, naphthyloxy, substituted naphthyloxy, heteroaryl, substituted heteroaryl, heteroaryloxy or substituted heteroaryloxy, wherein the heteroaryl or the heteroaryl group of heteroaryloxy is selected from thiophene, furan, pyridine, indole, chroman, coumarin, carbostyril, and quinoline;

$R^3$ is hydrogen or alkyl of 1 to 6 carbon atoms;

n is an integer from 0 to 6;

$R^4$ is hydrogen, alkyl of 1 to 6 carbon atoms, phenyl, substituted phenyl, ω-phenylalkyl, substituted ω-phenylalkyl, ω-diphenylalkyl, substituted ω-diphenylalkyl, wherein the alkyl chain contains 1 to 4 carbon atoms, indole, substituted indole, indazole, substituted indazole, pyridine, substituted pyridine, pyrimidine, substituted pyrimidine, quinoline, substituted quinoline, benzoisothiazole, substituted benzoisothiazole, benzisoxazole, or substituted benzisoxazole;

$R^5$ is hydrogen, hydroxy, cyano or carboxamido;

$R^6$ is hydrogen, 1-benzimidazol-2-one, benzoisothiazole, or benzisoxazole, each optionally substituted, or —Q—Ar;

Q is C=O, CHOH, or $(CH_2)_m$, m is an integer from 0 to 4;

Ar is phenyl optionally substituted; or $R^5$ and $R^6$, taken together with the carbon atom to which they are attached, form

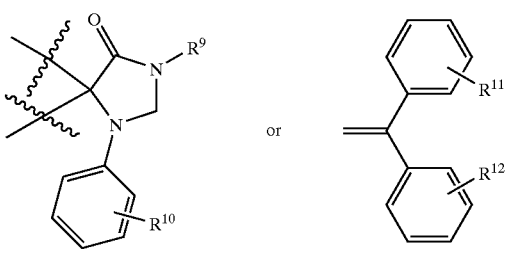

$R^7$ is hydrogen;

$R^8$ is phenyl, naphthyl, thiophene, benzoisothiazole, or benzisoxazole, each optionally substituted; or $R^7$ and $R^8$, taken together with the carbon atoms to which they are attached, form phenyl or substituted phenyl;

$R^9$ is hydrogen or alkyl of 1 to 6 carbon atoms; and $R^{10}$, $R^{11}$ and $R^{12}$ are, independently hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or a pharmaceutically acceptable salt thereof.

In some preferred embodiments of the invention $R^1$ is hydrogen, methoxy or halogen.

In other preferred embodiments of the invention, $R^2$ is hydrogen, alkyl of one to six carbon atoms, or trifluoromethyl.

In other preferred embodiments of the invention Z is $NR^3$—$(CH_2)_n$—Y.

Y is preferably phenyl or substituted phenyl.

$R^3$ is, in some aspects of the invention, preferably, hydrogen.

$R^4$ is preferably phenyl, indole, indazole, pyridine, pyrimidine, quinoline, benzoisothiazole, or benzisoxazole.

In certain preferred embodiments of the invention $R^5$ is hydrogen or hydroxy.

In other preferred embodiments of the invention $R^6$ is 1-benzimidazol-2-one, benzoisothiazole, benzisoxazole or Q—Ar.

Q is preferably C=O.

Preferably $R^7$ is hydrogen.

In other preferred embodiments of the invention $R^8$ is phenyl, benzoisothiazole, or benzisoxazole.

When taken together, $R^7$ and $R^8$ preferably form phenyl.

In certain preferred embodiments of the invention $R^1$ is hydrogen, methoxy or halo, $R^2$ is hydrogen, trifluoromethyl or alkyl of one to six carbon atoms, Z is $NR^3$—$(CH_2)_n$—Y and $R^3$ is hydrogen.

In some preferred embodiments of the invention, $R^2$ is hydrogen, alkyl of one to six carbon atoms or trifluoromethyl, Z is

and $R^4$ is phenyl, indole, indazole, pyridine, pyrimidine, quinoline, benzoisothiazole, or benzisoxazole, each optionally substituted. In more preferred embodiments of this invention $R^1$ is hydrogen, methoxy or halo, $R^2$ is hydrogen, trifluoromethyl or alkyl of one to six carbon atoms, Z is

and $R^4$ is phenyl, indole, indazole, pyridine, pyrimidine, quinoline, benzoisothiazole, or benzisoxazole, each optionally substituted.

In other preferred embodiments of the invention $R^2$ is hydrogen, alkyl of one to six carbon atoms or trifluoromethyl, Z is

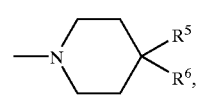

$R^5$ is hydrogen or hydroxy and $R^6$ is 1-benzimidazol-2-one, benzoisothiazole, or benzisoxazole, each optionally substituted. More preferably, $R^1$ is hydrogen, methoxy or halo, $R^2$ is hydrogen, alkyl of one to six carbon atoms or trifluoromethyl, Z is

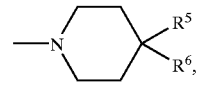

$R^5$ is hydrogen and $R^6$ is 1-benzimidazol-2-one, benzoisothiazole, or benzisoxazole, each optionally substituted.

In still other preferred embodiments of the invention $R^2$ is hydrogen, alkyl of one to six carbon atoms or trifluoromethyl, Z is

$R^5$ is hydrogen or hydroxy, $R^6$ is —Q—Ar, Q is C=O, and Ar is phenyl or substituted phenyl. More preferably, $R^1$ is hydrogen, methoxy or halo, $R^2$ is hydrogen, trifluoromethyl or alkyl of one to six carbon atoms, Z is

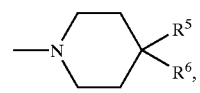

$R^5$ is hydrogen, $R^6$ is —Q—Ar, Q is C=O, and Ar is phenyl or substituted phenyl.

In yet other preferred embodiments of the invention $R^2$ is hydrogen, alkyl of one to six carbon atoms or trifluoromethyl, Z is

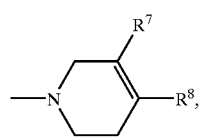

$R^7$ is hydrogen and $R^8$ is phenyl, benzoisothiazole, or benzisoxazole, each optionally substituted. More preferably $R^1$ is hydrogen, methoxy or halo, $R^2$ is hydrogen, trifluoromethyl or alkyl of one to six carbon atoms, Z is

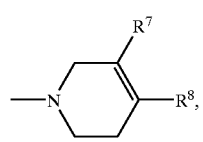

$R^7$ is hydrogen and $R^8$ is phenyl, benzoisothiazole, or benzisoxazole, each optionally substituted.

In other preferred embodiments of the invention, $R^2$ is hydrogen, alkyl of one to six carbon atoms or trifluoromethyl, Z is

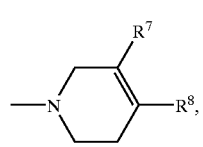

and $R^7$ and $R^8$, taken together with the carbon atoms to which they are attached form phenyl or substituted phenyl.

Still more preferably R¹ is hydrogen, methoxy or halo, R² is hydrogen, trifluoromethyl or alkyl of one to six carbon atoms, Z is

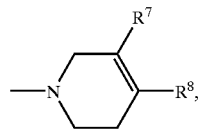

and R⁷ and R⁸, taken together with the carbon atoms to which they are attached form phenyl or substituted phenyl.

Where a substituent is "substituted" as used herein, e.g. substituted phenyl or substituted heteroaryl, it may include from 1 to 3 substituents the same or different selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

This invention relates to both the R and S stereoisomers of the 8-aminomethyl-7,8-dihydro-3H-6,9-dioxa-1,3-diaza-cyclopenta[a]naphthalene, as well as to mixtures of the R and S stereoisomers. Throughout this application, the name of the product of this invention, where the absolute configuration of the 8-aminomethyl-7,8-dihydro-3H-6,9-dioxa-1,3-diaza-cyclopenta[a]naphthalene is not indicated, is intended to embrace the individual R and S enantiomers as well as mixtures of the two. In some embodiments of the present invention the S stereoisomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Alkyl as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)₂—NH— where R is an alkyl group of 1 to 6 carbon atoms.

Alkoxy as used herein refers to the group R—O— where R is an alkyl group of 1 to 6 carbon atoms.

Carboxamido as used herein refers to the group —CO—NH₂.

Carboalkoxy as used herein refers to the group R—O—C(=O)— where R is an alkyl group of 1 to 5 carbon atoms.

Cycloalkyl refers to cyclic alkyl groups including mono-, bi- and polycyclic rings having from 3 to 15 carbon atoms. Representative examples include cyclohexyl and adamantyl.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention include:

(2-trifluoromethyl-7,8-dihydro-3H-6,9-dioxa-1,3-diaza-cyclopenta[a]naphthalen-8-yl)-methylamine;

(4-phenyl-butyl)-(2-trifluoromethyl-7,8-dihydro-3H-6,9-dioxa-1,3-diazacyclo-penta[a]naphthalen-8-ylmethyl)-amine;

benzyl-(2-trifluoromethyl-7,8-dihydro-3H-6,9-dioxa-1,3-diaza-cyclopenta[a]-naphthalen-8-ylmethyl)-amine;

8-(4-phenyl-5,6-dihydro-2H-pyridin-1-ylmethyl)-2-trifluoromethyl-7,8-dihydro-3H-6,9-diloxa-1,3-diaza-cyclopenta[a]naphthalene;

8-{[(adamant-1-ylmethyl)amino]-methyl}-2-trifluoromethyl-7,8-dihydro-3H-6,9-diioxa-1,3-diaza-cyclopenta[a]naphthalene;

8-(3,4,4a,8a-tetrahydro-1H-isoquinolin-2-ylmethyl)-2-trifluoromethyl-7,8-dihydro-3H-6,9-diioxa-1,3-diaza-cyclopenta[a]naphthalene;

8-[4-(4-fluorobenzoyl)-piperidin-1-ylmethyl]-2-trifluoromethyl-7,8-dihydro-3H-6,9-diioxa -1,3-diaza-cycopenta[a]naphthalene; and N-(3-(3-[(2-trifluoromethyl-7,8-dihydro-3H-6,9-diioxa-1,3-diazacyclopenta[a]-naphthalen-8-ylmethyl)-amino]-propoxy)-phenyl)-acetamide.

The 8-aminomethyl-7,8-dihydro-3H-6,9-dioxa-1,3-diazacyclopenta[a]-naphthalenes of the invention are prepared as illustrated below for examples in which Z is substituted piperazine. Specifically, the appropriately substituted nitroguaiacol is alkylated with allyl bromide in the presence of a suitable base such as sodium hydride and then demethylated by a reagent such as sodium hydroxide. The resulting 4-nitro-2-allyloxyphenol is then alkylated with glycidyl tosylate or an epihalohydrin in the presence of a base such as sodium hydride and heated in a high boiling solvent such as mesitylene or xylene to effect both rearrangement of the allyl group and cyclization of the dioxan ring. The resulting primary alcohol is converted to the tosylate by reaction with p-toluenesulfonyl chloride in the presence of a tertiary amine or pyridine, or alternatively to a halide by reaction with carbon tetrabromide or carbon tetrachloride in combination with triphenylphosphine. The allyl side chain is then isomerized by treatment with catalytic bis-acetonitrile palladium (II) chloride in refluxing methylene chloride or benzene and cleaved to the corresponding o-nitrobenzaldehyde by treatment with ozone followed by diisopropylethylamine or by catalytic osmium tetroxide in the presence of sodium periodate. The aldehyde is oxidized to the o-nitrobenzoic acid by a suitable oxidant such as chromium trioxide (Jones' oxidation) or sodium chlorite and the acid converted to the o-nitroaniline with diphenylphosphoryl azide (DPPA) in the presence of a

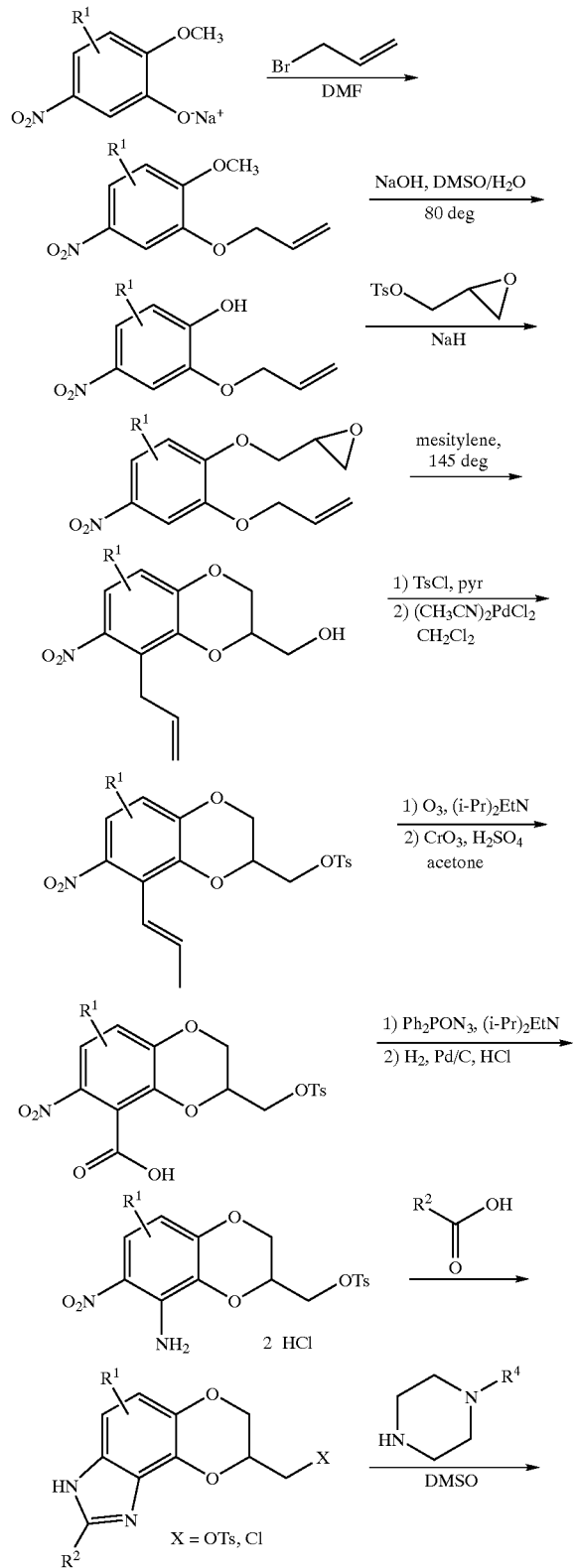

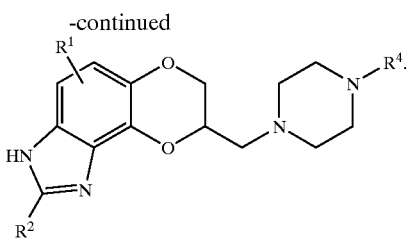

tertiary base such as diisopropylethylamine (Curtius reaction). Reduction of the resulting nitroaniline to the diamine with hydrogen and palladium on carbon and cyclization by treatment at reflux with the appropriate carboxylic acid gives the 7,8-dihydro-3H-6,9-dioxa-1,3-diaza-cyclopenta[a]naphthalene. Refluxing the diamine dihydrochloride in higher boiling carboxylic acids occasionally causes replacement of a tosylate group with a chloride. Replacement of the tosylate or halide with amines appropriate to the invention (Z—H) in some high boiling solvent such as dimethyl sulfoxide gives the title compounds of the invention in which $R^2$ is hydrogen or alkyl. Replacement of the halide or tosylate with sodium azide in hot DMF, followed by reduction by hydrogen over palladium on carbon gives the title compound in which Z is $NH_{2-}$.

Treatment of the diamine described above with cyanogen bromide or chloride or a suitably substituted carbamoyl chloride leads to compounds of the invention in which $R^2$ is amino. Treatment of the diamine with carbonyl diimidazole gives the imidazolone which leads to compounds of the invention in which $R^2$ is halo via treatment with an inorganic anhydride such as phosphoryl chloride or bromide, or to compounds of the invention in which $R^2$ is alkoxy by treatment with the appropriate alkylating agent. Replacement of the tosylate with the appropriately substituted amine as above gives the title compounds of the invention.

The o-nitrobenzaldehyde used in the Jones' oxidation described above may be alternatively prepared as shown below. The appropriate mono-allylated catechol is elaborated with glycidyl tosylate as described above and rearranged in refluxing mesitylene. Cyclization to the benzodioxan methanol is

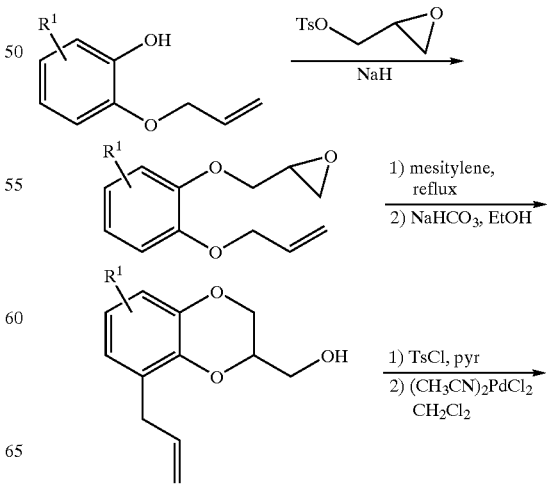

-continued

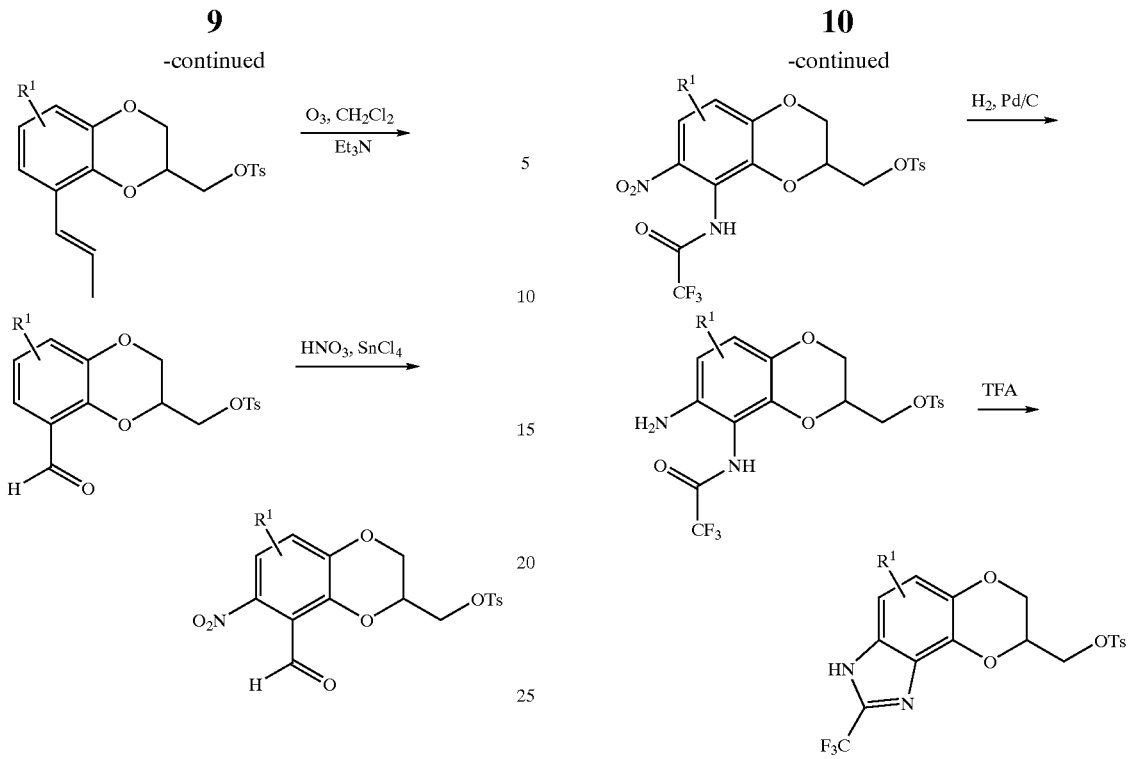

effected by treatment with sodium bicarbonate in ethanol and the alcohol is converted to the tosylate or halide as described above. After rearrangement of the double bond by treatment with catalytic bis-acetonitrile palladium (II) chloride in refluxing methylene chloride and cleavage with ozone or osmium tetroxide/sodium periodate as described above, the resulting aldehyde is regioselectively nitrated with a combination of nitric acid and tin (IV) chloride.

Compounds of the invention in which $R^2$ is trifluoromethyl may also be conveniently prepared from the nitroaniline described above by the procedure illustrated below. The nitroaniline is treated with trifluoroacetic anhydride in the presence of a suitable tertiary base such as diisopropylethylamine to yield the o-nitrophenyl trifluoroacetamide. This intermediate is reduced to the o-anilino trifluoroacetamide by treatment with hydrogen over palladium on carbon and cyclized to the trifluoromethylimidazole in refluxing trifluoroacetic acid. Replacement of the tosylate with the appropriately substituted amine as above gives the title compounds of the invention.

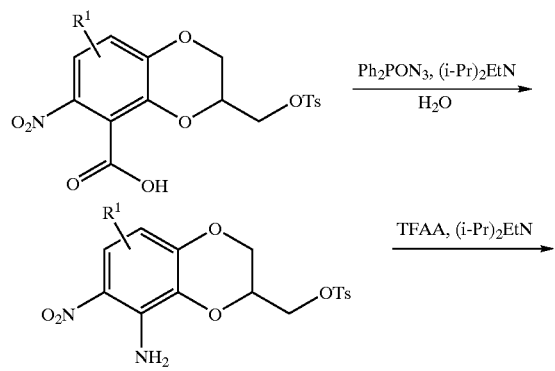

The guaiacols, catechols and amines appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epihalohydrin or racemic glycidyl tosylate in the procedures above.

The antipsychotic activity of the compounds of the invention was established by a determination of functional antagonism of dopamine receptors in vivo, specifically the compounds' ability to reduce mouse locomotor activity according to the method of Martin and Bendensky, J. Pharmacol. Exp. Therap. 229: 706–711, 1984, in which mice (male, CF-1, Charles River, 20–30 g) were injected with vehicle or various doses of each drug and locomotor activity was measured for 30 minutes using automated infrared activity monitors (Omnitech—8×8 inch open field) located in a darkened room. $ED_{50}$'s were calculated from the horizontal activity counts collected from 10 to 20 minutes after dosing using a nonlinear regression analysis with inverse prediction. When examined in this assay, the compounds of this invention, with the exception of example 1, produce $ED_{50}$'s of less than 50 mg/kg, sc.

Affinity for the dopamine $D_2$ receptor was established by a modification of the standard experimental test procedure of Seemen and Schaus, European Journal of Pharmacology 203: 105–109, 1991, wherein homogenized rat striatal brain tissue is incubated with $^3$H-quinpirole and various concentrations of test compound, filtered and washed and counted in a Betaplate scintillation counter. The results of this testing with compounds representative of this invention are given below.

| Compound | D$_2$ Receptor Affinity (IC$_{50}$ (nM)) |
| --- | --- |
| Example 1 | 260 |
| Example 2 | 0.40 |
| Example 3 | 2.20 |

The compounds of the invention are partial agonists at the D$_2$ sub-family of dopamine receptors. At presynaptic dopamine receptors, the compounds of the invention are autoreceptor agonists; that is, they serve to modulate the synthesis and release of the neurotransmitter dopamine. At postsynaptic dopamine receptors, these compounds are capable of functioning as either agonists or antagonists depending on the level of dopaminergic stimulation. They thus serve to modulate dopaminergic neurotransmission and are thereby useful for treatment of disorders of the dopaminergic system, such as schizophrenia, schizoaffective disorder, bipolar disorder, Parkinson's disease, L-DOPA induced pychoses and dyskinesias, Tourette's syndrome and hyperprolactinemia and in the treatment of drug addiction such as the addiction to ethanol, nicotine or cocaine and related illnesses.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 10 mg per day with gradual increase in the daily dose to about 200 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug" as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

INTERMEDIATE 1

3-Allyloxy-4-methoxynitrobenzene 97.5 g (0.51 mole) of the sodium salt of 5-nitroguaiacol was dissolved in one liter of N,N-dimethylformamide and 1.5 equivalents of allyl bromide added. The reaction was heated to 65° C. for two hours, after which time much of the dark color had discharged and tlc (1:1 methylene chloride/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93–94° C.

INTERMEDIATE 2

2-Allyloxy-4-nitrophenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tlc 1:1 methylene chloride/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61–62° C. The aqueous mother liquors from the initial crystallization above were extracted with 2 L of ethyl acetate. This was dried over sodium sulfate, filtered and evaporated to a dark oil. Column chromatography on silica with 1:1 methylene chloride/hexane gave an additional 12 g of the title compound as a yellow solid. Elution with 2% methanol in chloroform gave 12 g of a dark oil which slowly crystallized in vacuum. This proved to be the Claisen product, 3-allyl-4-nitrocatechol.

INTERMEDIATE 3

2-(2-Allyoxy-4-nitrophenoxymethyl)-oxirane 20 g (0.50 mole) of 60% NaH/mineral oil was placed in a two liter flask and washed with 500 mL of hexane. 1 L of N,N-dimethylformamide was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the N,N-dimethylformamide was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tic with 1:1 hexane/methylene chloride) (R)-2-(2-allyoxy-4-nitrophenoxymethyl)-oxirane (m.p. 64° C.).

Elemental Analysis for: $C_{12}H_{13}NO_5$
Calc'd: C, 57.37; H, 5.21; N, 5.58
Found: C, 57.50; H, 5.21; N, 5.43

INTERMEDIATE 4

(8-Allyl-7-nitro-2,3-dihydro-benzo(1,4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$
Calc'd: C, 57.37; H, 5.21; N, 5.58
Found: C, 57.26; H, 5.20; N, 5.35

INTERMEDIATE 5

Toluene-4-sulfonic Acid 8-allyl-7-nitro-2,3-dihydro-benzo(1,4)-dioxin-2-ylmethyl Ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$
Calc'd: C, 56.29; H, 4.72; N, 3.45
Found: C, 56.13; H, 4.58; N, 3.44

INTERMEDIATE 6

{7-Nitro-8-[1-propenyl]-2,3-dihydro-1,4-benzodioxin-2-yl}methyl 4-methylbenzenesulfonate To a solution of 10.0 g (24.0 mmole) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluant gave 7.2 g of the title compound as a mixture of E and Z isomers. A sample of {(2R)-7-nitro-8[(E)-1-propenyl]-2,3-dihydro-1,4-benzodioxin-2-yl}methyl 4-methylbenzenesulfonate was obtained as a yellow solid (m.p. 105–106° C.) by evaporation of a pure E isomer-containing fraction.

Elemental Analysis for: $C_{19}H_{19}NO_7S$

Calc'd: C, 56.29; H, 4.72; N, 3.45
Found: C, 56.12; H, 4.64; N, 3.39

INTERMEDIATE 7

(8-Formyl-7-nitro-2,3-dihydro-1,4-benzodioxin-2-yl) methyl 4-methylbenzenesulfonate {(2R)-7-Nitro-8-[1-propenyl]-2,3-dihydro-1,4-benzodioxin-2-yl}methyl 4-methylbenze (10.5 g, 25.9 mmole) dissolved in 400 mL of methylene chloride was treated with excess ozone at −78° C. Diisopropylethylamine (11.5 mL, 66.0 mmole) was then added dropwise over 30 min and the mixture allowed to come to room temperature and stir overnight under a nitrogen atmosphere. The mixture was then diluted to 600 mL with methylene chloride, washed three times with 100 mL portions of 2N HCl (aq), twice with 200 mL portions of saturated aqueous sodium bicarbonate and with 200 mL of saturated brine. The solution was dried over magnesium sulfate, filtered and concentrated in vacuum to a crude brown oil, which was column chromatographed on silica gel with 10% hexane/methylene chloride to give 7.52 g of the (R)-enantiomer of the title compound as a yellow solid. $^1$H-NMR (CDCl$_3$): doublet 7.8 δ (2H); doublet 7.62 δ (1H); doublet 7.4 δ (2H); doublet 7.0 δ (1H); multiplet 4.4-4.6 δ (2H); multiplet 4.2 δ (3H); singlet 2.4 δ (3H).

INTERMEDIATE 8

6-Nitro-3-(toluene-4-sulfonlyloxymethyl)-2,3-dihydro-benzo[1,4]dioxin-5-yl) carboxylic acid The oxidation reagent was prepared by dissolving 7.0 g (70 mmole) of chromium trioxide in 10 mL of water in a 50 mL beaker. The beaker was immersed in an ice bath and 6.1 mL (110 mmoles) of concentrated sulfuric acid added, followed by 20 mL additional water. The oxidant was added dropwise to a solution of (2R)-(8-formyl-7-nitro-2,3-dihydro-1,4-benzodioxin-2-yl)methyl 4-methylbenzenesulfonate (12.4 g, 30.6 mmole) dissolved in 100 mL of acetone and cooled in an ice bath. The mixture was stirred at room temperature for 3 hours after the addition was complete. Sodium bisulfite was then added in small portions until the brown color was gone. The mixture was diluted to 500 mL with water and extracted twice with 300 mL portions of ethyl acetate. The combined extracts were washed with 300 mL of water and with 300 mL of saturated brine, dried over sodium sulfate, filtered and evaporated to 13.4 g of the (R)-enantiomer of the title compound as a viscous yellow oil.

$^1$H-NMR (CDCl$_3$): 2 superimposed doublets 7.8 δ (3H); doublet 7.4 δ (2H); doublet 7.0 δ (1H); multiplet 4.55 δ (1H); doublet 4.45 δ (1H); multiplet 4.25 δ (3H); singlet 2.4 δ (3H).

INTERMEDIATE 9

Toluene-4-sulfonic Acid 8-amino-7-nitro-2,3-dihydro-benzo(1,4)dioxin-2-ylmethyl Ester To 7.0 g (17 mmole) of (S)-6-nitro-3-(toluene-4-sulfonyloxymethyl)-2,3-dihydro-benzo[1,4]dioxin-5-yl) carboxylic acid in 250 mL of tetrahydrofuran was added 9.4 g (34 mmole) of diphenylphosphoryl azide and 5.2 g (40 mmole) of diisopropylethylamine and the mixture was refluxed under nitrogen for 24 hours. Water (3 mL) was added and the mixture refluxed under nitrogen overnight. The reaction was diluted to 600 mL with ethyl acetate and washed with 300 mL portions of 1 N HCl, saturated aqueous sodium bicarbonate and saturated brine. The mixture was then dried over sodium sulfate, filtered and concentrated in vacuum and the residue column chromatographed on silica gel with methylene chloride as eluant to give 4.1 g of the (R)-enantiomer of the title compound as a yellow solid (m.p. 155° C.).

Elemental Analysis for: $C_{16}H_{16}N_2O_7S$
Calc'd: C, 50.52; H, 4.24; N, 7.36
Found: C, 50.27; H, 3.99; N, 7.23

INTERMEDIATE 10

[7,8-Diamino-2,3-dihydro-1,4-benzodioxin-2-yl] methyl 4-methylbenzenesulfonate

Toluene-4-sulfonic acid (2R)-8-amino-7-nitro-2,3-dihydro-benzo(1,4)dioxin-2-ylmethyl ester (4.1 g, 11 mmole) was dissolved in 200 mL of methanol to which 0.50 g of 10% palladium on carbon had been added. 4 N isopropanol HCl (10 mL) was then added and the mixture treated with 60 psi of hydrogen on a Parr apparatus overnight. The mixture was filtered through celite and concentrated in vacuum to give 4.6 g of the (R)-enantiomer of the title compound as a pink solid dihydrochloride (m.p. 178–180° C.).

Elemental Analysis for: $C_{16}H_{18}N_2O_5S.2$ HCl
Calc'd: C, 45.40; H, 4.76; N, 6.62
Found: C, 45.06; H, 4.63; N, 6.47

INTERMEDIATE 11

(2-Trifluoromethyl-7,8-dihydro-3H-6,9-dioxa-1,3-diaza-cyclopenta[a]naphthalen-8-yl)methyl 4-methylbenzenesulfonate A solution of 3.1 g (7.3 mmole) of [(2R)-7,8-diamino-2,3-dihydro-1,4-benzodioxin-2-yl]methyl 4-methylbenzenesulfonate dihydrochloride in 50 mL of trifluoroacetic acid was refluxed under nitrogen for 6 hours. The mixture was diluted to 400 mL with methylene chloride, washed with 400 mL of water and with 400 mL of saturated aqueous sodium bicarbonate, dried over magnesium sulfate, filtered and concentrated to a crude foam in vacuum. The crude product was column chromatographed on silica gel with 1% methanol in chloroform and the product fractions combined and concentrated in vacuum to give 3.3 g of the (R)-enantiomer of the title compound as a white solid (m.p. 114–116° C.), which retains one equivalent of chloroform.

Elemental Analysis for: $C_{18}H_{15}F_3N_2O_5S.CHCl_3$
Calc'd: C, 41.66; H, 2.94; N, 5.11
Found: C, 41.74; H, 2.76; N, 5.11

EXAMPLE 1

(2-Trifluoromethyl-7,8-dihydro-3H-6,9-dioxa-1,3-diaza-cyclopenta[a]naphthalen-8-yl)-methylamine A mixture of 5.0 g (12 mmole) of [(8R)-2-trifluoromethyl-7,8-dihydro-3H-6,9-dioxa-1,3-diaza-cyclopenta[a]naphthalen-8-yl]methyl 4-methylbenzenesulfonate and 1.3 g (20 mmole) of sodium azide were dissolved in 300 mL of N,N-dimethylformamide and heated at 85° C. for 15 hours. The solvent was removed in vacuum and replaced with 500 mL of methylene chloride. The mixture was washed with two 500 mL portions of water and with 500 mL of saturated brine, dried over sodium sulfate, filtered and concentrated in vacuum. The crude residue was dissolved in 200 mL of methanol and added to a slurry of 0.50 g of 10% palladium on carbon in methanol in a 500 mL hydrogenation bottle. The mixture was treated with 50 psi of hydrogen on a Parr shaker for 15 hours. The catalyst was removed by filtration through celite and the filtrate concentrated in vacuum. The crude residue was column chromatographed on silica gel with 10% methanol in chloroform and the product fractions were combined and concentrated in vacuum, and the product recrystallized from ethanol to give 2.0 g of the (S)-enantiomer of the title column as a white solid, m.p. 199–201° C.

Elemental Analysis for: $C_{11}H_{10}F_3N_3O_2 \cdot 0.5\ H_2O$

Calc'd: C, 46.81; H, 3.93; N, 14.89

Found: C, 46.96; H, 3.59; N, 14.67

EXAMPLE 2

(4-Phenyl-butyl)-(2-trifluoromethyl-7,8-dihydro-3H-6,9-dioxa-1,3-diaza-cyclopenta[a]naphthalen-8-ylmethyl)-amine A mixture of 0.50 g (1.2 mmole) of [(8R)-2-trifluoromethyl-7,8-dihydro-3H-6,9-dioxa-1,3-diaza-cyclopenta[a]naphthalen-8-yl]methyl 4-methylbenzenesulfonate and 0.75 g (5.0 mmole) of 4-phenylbutylamine in 25.0 mL of DMSO was heated at 80–90° C. under nitrogen for 4 hours. The reaction was allowed to come to room temperature, diluted to 500 mL with ethyl acetate, washed with 500 mL portions of saturated aqueous sodium bicarbonate and water, dried over sodium sulfate, filtered and evaporated in vacuum. The residue was column chromatographed on silica gel with 2% methanol in chloroform as eluant and the product fractions evaporated to give 0.24 g of the desired product. This was recrystallized from ethanol with the addition of oxalic acid to give 0.092 g of the (S)-enantiomer of the title compound as a white solid oxalate, hydrate, m.p. 124–127° C.

Elemental Analysis for: $C_{21}H_{22}F_3N_4O_2 \cdot C_2H_2O_4 \cdot H_2O$

Calc'd: C, 53.80; H, 5.10; N, 8.18

Found: C, 54.03; H, 4.80; N, 7.69

EXAMPLE 3

Benzyl-(2-trifluoromethyl-7,8-dihydro-3H-6,9-dioxa-1,3-diaza-cyclopenta[a]naphthalen-8-ylmethyl)-amine A mixture of 0.60 g (1.4 mmole) of [(8R)-2-trifluoromethyl-7,8-dihydro-3H-6,9-dioxa-1,3-diaza-cyclopenta[a]naphthalen-8-yl]methyl 4-methylbenzenesulfonate and 1.07 g (10.0 mmole) of benzylamine in 40.0 mL of DMSO was heated at 80° C. under nitrogen for 4 hours. The reaction was allowed to come to room temperature, diluted to 400 mL with ethyl acetate, washed with 400 mL portions of saturated aqueous sodium bicarbonate, water and saturated brine, dried over sodium sulfate, filtered and evaporated in vacuum. The residue was column chromatographed on silica gel with 2% methanol in chloroform as eluant and the product fractions concentrated in vacuum and the residue recrystallized from ethanol with the addition of oxalic acid gave 0.34 g of the (S)-enantiomer of the title compound as a white solid oxalate, one-quarter hydrate, m.p. 2490C.

Elemental Analysis for: $C_{18}H_{16}F_3N_3O_2 \cdot C_2H_2O_4 \cdot 0.25H_2O$

Calc'd: C, 52.46; H, 4.07; N, 9.18

Found: C, 52.29; H, 3.85; N, 8.83

EXAMPLE 4

8-(4-Phenyl-5,6-dihydro-2H-pyridin-1-ylmethyl)-2-trifluoromethyl-7,8-dihydro-3H-6,9-diioxa-1,3-diaza-cyclopenta[a]naphthalene A mixture of 0.50 g (1.2 mmole) of [(8R)-2-trifluoromethyl-7,8-dihydro-3H-6,9-dioxa-1,3-diaza-cyclopenta[a]naphthalen-8-yl]methyl 4-methylbenzenesulfonate and 1.0 g (6.2 mmole) of 4-phenyl-1,2,3,6-tetrahydropyridine in 10.0 mL of DMSO was heated at 85° C. under nitrogen for 6 hours. The reaction was allowed to come to room temperature, diluted to 400 mL with ethyl acetate, washed with 400 mL portions of saturated aqueous sodium bicarbonate, water and saturated brine, dried over sodium sulfate, filtered and evaporated in vacuum. The residue was column chromatographed on silica gel with 1% methanol in chloroform as eluant and the product fractions concentrated in vacuum to give the desired compound as the free base. Recrystallization from ethanol with the addition of 4N HCl/IPA gave 86 mg of the (S)-enantiomer of the title compound as a hydrochloride hydrate.

Elemental Analysis for: $C_{22}H_{20}F_3N_3O_2 \cdot HCl \cdot 0.5H_2O$, m.p. 195–8° C.

Calc'd: C, 57.33; H, 4.81; N, 9.12

Found: C, 57.21; H, 4.65; N, 8.83

EXAMPLE 5

8-{[(Adamant-1-ylmethyl)amino]-methyl}-2-trifluoromethyl-7,8-dihydro-3H-6,9-diioxa-1,3-diaza-cyclopenta[a]naphthalene A mixture of 0.50 g (1.2 mmole) of [(8R)-2-trifluoromethyl-7,8-dihydro-3H-6,9-dioxa-1,3-diaza-cyclopenta[a]naphthalen-8-yl]methyl 4-methylbenzenesulfonate and 1.0 g (6.1 mmole) of 1-adamantanemethylamine in 10.0 mL of DMSO was heated at 85° C. under nitrogen for 6 hours. The reaction was allowed to come to room temperature, diluted to 400 mL with ethyl acetate, washed with 400 mL portions of saturated aqueous sodium bicarbonate, water and saturated brine, dried over sodium sulfate, filtered and evaporated in vacuum. The residue was column chromatographed on silica gel with 1% methanol in chloroform as eluant and the product fractions concentrated in vacuum to give the desired compound as the free base. Recrystallization from ethanol with the addition of 4N HCl/IPA gave 0.18 g of the (S)-enantiomer of the title compound as a hydrochloride, hydrate, m.p. 207–210° C.

Elemental Analysis for: $C_{22}H_{26}F_3N_3O_2 \cdot HCl \cdot H_2O$

Calc'd: C, 55.52; H, 6.14; N, 8.83

Found: C, 55.68; H, 5.94; N, 8.79

EXAMPLE 6

8-(3,4,4a,8a-Tetrahydro-1H-isoguinolin-2-ylmethyl)-2-trifluoromethyl-7,8-dihydro-3H-6,9-diioxa-1,3-diaza-cyclopenta[a]naphthalene A mixture of 0.50 g (1.2 mmole) of [(8R)-2-trifluoromethyl-7,8-dihydro-3H-6,9-dioxa-1,3-diaza-cyclopenta[a]naphthalen-8-yl]methyl 4-methylbenzenesulfonate and 1.0 g (7.5 mmole) of 1,2,3,4-tetrahydroisoquinoline in 10.0 mL of DMSO was heated at 85° C. under nitrogen for 6 hours. The reaction was allowed to come to room temperature, diluted to 400 mL with ethyl acetate, washed with 400 mL portions of saturated aqueous sodium bicarbonate, water and saturated brine, dried over sodium sulfate, filtered and evaporated in vacuum. The residue was column chromatographed on silica gel with 1% methanol in chloroform as eluant and the product fractions concentrated in vacuum to give the desired compound as the free base. Recrystallization from isopropanol with the addition of 4N HCl/IPA gave 0.16 g of the (S)-enantiomer of the title compound as a hydrochloride, m.p. 158–165° C., retaining water and isopropanol.

Elemental Analysis for: $C_{20}H_{18}F_3N_3O_2 \cdot HCl \cdot 0.5 C_3H_8O \cdot 1.5 H_2O$ Calc'd: C, 53.48; H, 5.43; N, 8.70

Found: C, 53.20; H, 5.05; N, 8.65

EXAMPLE 7

8-[4-(4-Fluorobenzoyl)-piperidin-1-ylmethyl]-2-trifluoromethyl-7,8-dihydro-3H-6,9-diioxa-1,3-diaza-cyclopenta[a]naphthalene A mixture of 0.50 g (1.2 mmole) of [(8R)-2-trifluoromethyl-7,8-dihydro-3H-6,9-dioxa-1,3-diaza-cyclopenta[a]naphthalen-8-yl]methyl 4-methylbenzenesulfonate and 1.0 g (4.8 mmole) of 4-(4-fluorobenzoyl)piperidine in 10.0 mL of DMSO was heated at 85° C. under nitrogen for 6 hours. The reaction was allowed to come to room temperature, diluted to 400 mL with ethyl acetate, washed with 400 mL portions of saturated aqueous sodium bicarbonate, water and saturated brine, dried over sodium sulfate, filtered and evaporated in vacuum. The residue was column chromatographed on silica gel with 1% methanol in chloroform as eluant and the product fractions concentrated in vacuum to give the desired compound as the free base. Recrystallization from ethanol with the addition of 4N HCl/IPA gave 0.18 g of the (S)-enantiomer of the title compound as a yellow hydrochloride, m.p. 195–200° C.

Elemental Analysis for: $C_{23}H_{21}F_4N_3O_3 \cdot HCl$

Calc'd: C, 55.26; H, 4.44; N, 8.41

Found: C, 55.67; H, 4.70; N, 7.84

EXAMPLE 8

N-(3-(3-[(2-Trifluoromethyl-7,8-dihydro-3H-6,9-diioxa-1,3-diaza-cyclopenta[a]naphthalen-8-ylmethyl)-amino]-propoxy)-phenyl)-acetamide A mixture of 0.50 g (1.2 mmole) of [(8R)-2-trifluoromethyl-7,8-dihydro-3H-6,9-dioxa-1,3-diaza-cyclopenta[a]naphthalen-8-yl]methyl 4-methylbenzenesulfonate and 1.0 g (4.8 mmole) of N-[3-(3-amino-propoxy)-phenyl]-acetamide in 10.0 mL of DMSO was heated at 85° C. under nitrogen for 6 hours. The reaction was allowed to come to room temperature, diluted to 400 mL with ethyl acetate, washed with 400 mL portions of saturated aqueous sodium bicarbonate, water and saturated brine, dried over sodium sulfate, filtered and evaporated in vacuum. The residue was column chromatographed on silica gel with 10% ethyl acetate in methylene chloride as eluant and the product fractions concentrated in vacuum to give 0.22 g of the (S)-enantiomer of the title compound as a yellow solid, m.p. 103–107° C., containing 0.4 moles of ethyl acetate.

Elemental Analysis for: $C_{22}H_{23}F_3N_4O_4 \cdot 0.4 C_4H_8O_2$

Calc'd: C, 56.73; H, 5.29; N, 11.21

Found: C, 56.54; H, 5.35; N, 10.82

EXAMPLE 9

1-Phenyl-8-{[2-(trifluoromethyl)-7,8-dihydro-3H-[1,4]dioxino[2,3-e]-benzimidazol-8-yl[methyl]-1,3,8-triazaspiro[4,5]decan-4-one A mixture of 0.50 g (1.2 mmole) of [(8R)-2-trifluoromethyl-7,8-dihydro-3H-6,9-dioxa-1,3-diaza-cyclopenta[a]naphthalen-8-yl]methyl 4-methylbenzenesulfonate and 0.92 g (4.0 mmole) of 1-phenyl-1,3,6-triazaspiro[4,5]decan-4-one in 10.0 mL of DMSO was heated at 85° C. under nitrogen for 6 hours. The reaction was allowed to come to room temperature, diluted to 400 mL with ethyl acetate, washed with 400 mL portions of saturated aqueous sodium bicarbonate, water and saturated brine, dried over sodium sulfate, filtered and evaporated in vacuum. The residue was column chromatographed on silica gel with 1% methanol in chloroform as eluant and the product fractions combined using ethyl acetate as solvent and concentrated in vacuum to give 0.22 g of the (S)-enantiomer of the title compound as an off-white solid, m.p. 185–190° C., which retains 0.50 moles each of water and ethyl acetate.

Elemental Analysis for: $C_{24}H_{24}F_3N_5O_3 \cdot 0.5 H_2O \cdot 0.5 C_4H_8O_2$ Calc'd: C, 57.77; H, 5.41; N, 12.96

Found: C, 57.53; H, 5.03; N, 13.06

What is claimed is:

1. A compound of formula I:

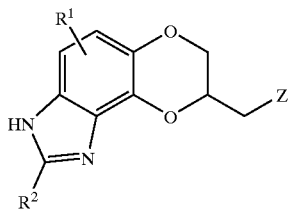

wherein

R1 and R2 are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

Z is $NR^3—(CH_2)_n—Y$,

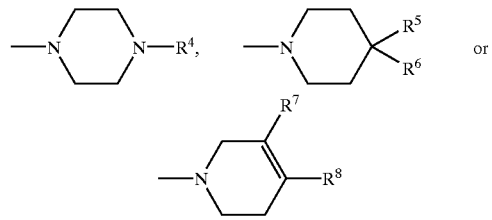

wherein,

Y is hydrogen, hydroxy, cycloalkyl of 3 to 15 carbon atoms, or phenyl, phenoxy, naphthyl, naphthyloxy, heteroaryl, or heteroaryloxy, wherein the heteroaryl or the heteroaryl group of heteroaryloxy is selected from thienyl, furanyl, pyridinyl, indolyl, chromanyl, coumarinyl, carbostyrilyl, and quinolinyl;

$R^3$ is hydrogen or alkyl of 1 to 6 carbon atoms;

n is an integer from 0 to 6;

R4 is hydrogen, alkyl of 1 to 6 carbon atoms, phenyl, ω-phenylalkyl, ω-diphenylalkyl, wherein the alkyl chain contains 1 to 4 carbon atoms, indolyl, indazolyl, pyridinyl, pyrimidinyl, quinolinyl, beuzoisothiazolyl, or benzisoxazolyl;

R5 is hydrogen, hydroxy, cyano or carboxamido;
R6 is hydrogen, 1-benzimidazol-2-onyl, benzoisothiazole, or benzisoxazolyl, or —Q—Ar;
Q is C=O, CHOH, or (CH$_2$)m,
m is an integer from 0 to 4;
Ar is phenyl; or
R$^5$ and R$^6$, taken together with the carbon atom to which they are attached, form

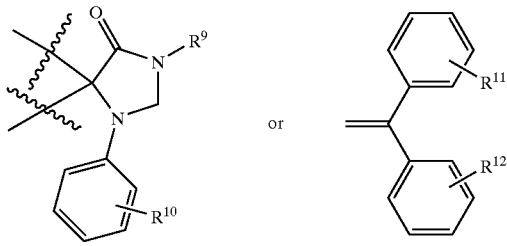

R$^7$ is hydrogen;
R$^8$ is phenyl, naphthyl, thienyl, benzoisothiazolyl, or benzisoxazolyl; or
R$^7$ and R$^8$, taken together with the carbon atoms to which they are attached, form a benzene ring;
R$^9$ is hydrogen or alkyl of 1 to 6 carbon atoms; and
R$^{10}$, R$^{11}$ and R$^{12}$ are, independently hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or a pharmaceutically acceptable salt thereof;
wherein said phenyl, phenoxy, naphthyl, naphthyloxy, heteroaryloxy, ω-phenylalkyl, ω-diphenylalkyl, indolyl, indazolyl, pyridinyl, pyrimidinyl, quinolinyl, benzoisothiazolyl, benzisoxazolyl, 1-benzimidazol-2-onyl, or thienyl groups, or the benzene ring, are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms. Alkanoyloxy of 2 to 6 carbon atoms, amino, mono- or di-alkylamino in which each alkyl around has 1 to 6 carbon atoms, alkanamido of 2 to 6 carbon atoms, or alkanesulfonamido of 1 to 6 carbon atoms.

2. A compound of claim 1 wherein R$^1$ is hydrogen, methoxy or halogen.

3. A compound of claim 1 wherein R$^2$ is hydrogen, alkyl of one to six carbon atoms, or trifluoromethyl.

4. A compound of claim 1 wherein Z is NR$^3$—(CH$_2$)$_n$—Y.

5. A compound of claim 4 wherein Y is phenyl or substituted phenyl.

6. A compound of claim 1 wherein R$^3$ hydrogen.

7. A compound of claim 1 wherein R$^4$ is phenyl, indolyl, indazolyl, pyridinyl, pyrimidinyl, quinolinyl, benzoisothiazolyl, or benzisoxazolyl.

8. A compound of claim 1 wherein R$^5$ is hydrogen or hydroxy.

9. A compound of claim 1 wherein R$^6$ is 1-benzimidazol-2-onyl, benzoisothiazolyl, or benzisoxazolyl or Q—Ar.

10. A compound of claim 9 wherein Q is C=.

11. A compound of claim 1 wherein R$^7$ is hydrogen.

12. A compound of claim 1 wherein R$^8$ is phenyl, benzoisothiazolyl, or benzisoxazolyl.

13. A compound of claim 1 wherein R$^7$ and R$^8$, taken together form a benzene ring.

14. A compound of claim 1 wherein R$^1$ is hydrogen, methoxy or halo, R$^2$ is hydrogen, trifluoromethyl or alkyl of one to six carbon atoms, Z is NR$^3$—(CH$_2$)$_n$—Y and R$^3$ is hydrogen.

15. A compound of claim 1 wherein R$^2$ is hydrogen, alkyl of one to six carbon atoms or trifluoromethyl, Z is

and R$^4$ is phenyl, indolyl, indazolyl, pyridinyl, pyrimidinyl, quinolinyl, benzoisothiazolyl, or benzisoxazolyl, each optionally substituted.

16. A compound of claim 15 wherein R$^1$ is hydrogen, methoxy or halogen.

17. A compound of claim 1 wherein R$^2$ is hydrogen, alkyl of one to six carbon atoms or trifluoromethyl, Z is

R$^5$ is hydrogen or hydroxy and R$^6$ is 1-benzimidazol-2-onyl, benzoisothiazolyl, or benzisoxazolyl, each optionally substituted.

18. A compound of claim 17 wherein R$^1$ is hydrogen, methoxy or halogen and R$^5$ is hydrogen.

19. A compound of claim 1 wherein R$^2$ is hydrogen, alkyl of one to six carbon atoms or trifluoromethyl, Z is

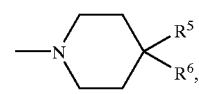

R$^5$ is hydrogen or hydroxy, R$^6$ is—Q—Ar, Q is C=O, and Ar is phenyl or substituted phenyl.

20. A compound of claim 19 wherein R$^1$ is hydrogen, methoxy or halogen, and R$^5$ is hydrogen.

21. A compound of claim 1 wherein R$^2$ is hydrogen, alkyl of one to six carbon atoms or trifluoromethyl, Z is

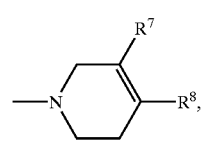

R$^7$ is hydrogen and R$^8$ is phenyl, beuzoisothiazolyl, or benzisoxazolyl, each optionally substituted.

22. A compound of claim 21 wherein R$^1$ is hydrogen, methoxy or halogen.

23. A compound of claim 1 wherein R$^2$ is hydrogen, alkyl of one to six carbon atoms or trifluoromethyl, Z is

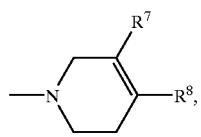

and R[7] and R[8], taken together with the carbon atoms to which they are attached form a benzene ring or a substituted benzene ring.

24. A compound of claim 23 wherein R[1] is hydrogen, methoxy or halogen.

25. The compound of claim 1 which is (2-trifluoromethyl-7,8-dihydro-3H-6,9-dioxa-1,3-diaza-cyclopenta[a]naphthalen-8-yl)-methylamine or a pharmaceutically acceptable salt thereof.

26. The compound of claim 1 which is (4-phenyl-butyl)-(2-trifluoromethyl-7,8-dihydro-3H-6,9-dioxa-1,3-diaza-cyclopenta[a]naphthalen-8-ylmethyl)-amine or a pharmaceutically acceptable salt thereof.

27. The compound of claim 1 which is benzyl-(2-trifluoromethyl-7,8-dihydro-3H-6,9-dioxa-1, 3-diaza-cyclopenta[a]naphthalen-8-ylmethyl)-amine or a pharmaceutically acceptable salt thereof.

28. The compound of claim 1 which is 8-(4-phenyl-5,6-dihydro-2H-pyridin-1-ylmethyl)-2-trifluoromethyl-7,8-dihydro-3H-6,9-diioxa-1,3-diaza-cyclopenta[a]-naphthalene or a pharmaceutically acceptable salt thereof.

29. The compound of claim 1 which is 8-{[(adamant-1-ylmethyl)amino]-methyl}-2-trifluoromethyl-7,8-dihydro-3H-6,9-diioxa-1,3-diaza-cyclopenta[a]-naphthalene or a pharmaceutically acceptable salt thereof.

30. The compound of claim 1 which is 8-(3,4,4a,8a-tetrahydro-1H-isoquinolin-2-ylmethyl)-2-trifluoromethyl-7,8-dihydro-3H-6,9-diioxa-1,3-diaza-cyclopenta[a]-naphthalene or a pharmaceutically acceptable salt thereof.

31. The compound of claim 1 which is 8-[4-(4-fluorobenzoyl)-piperidin-1-ylmethyl]-2-trifluoromethyl-7,8-dihydro-3H-6,9-diioxa-1,3-diaza-cyclopenta[a]-naphthalene or a pharmaceutically acceptable salt thereof.

32. The compound of claim 1 which is N-(3-(3-[(2-trifluoromethyl-7,8-dihydro-3H-6,9-diioxa-1,3- diaza-cyclopenta[a]naphthalen-8-ylmethyl)-amino]-propoxy)-phenyl)-acetamide or a pharmaceutically acceptable salt thereof.

33. A method of treating a subject suffering from a condition selected from schizophrenia, schizoaffective disorder, bipolar disorder, Parkinson's disease, L-DOPA induced psychoses or dyskinesias, Tourette's syndrome or hyperprolactinemia which comprises providing to the subject suffering from said condition, a therapeutically effective amount of a compound of formula I:

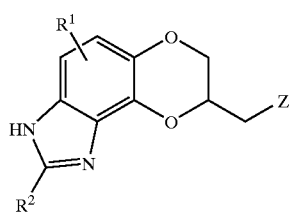

wherein
R[1] and R[2] are, independently, hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, ammo, mono- or di-alkylamino in which each alkyl group has 1 to 6 carbon atoms, alkanamido of 2 to 6 carbon atoms, or alkanesulfonamido of 1 to 6 carbon atoms;

Z is $NR^3$—$(CH_2)_n$—Y,

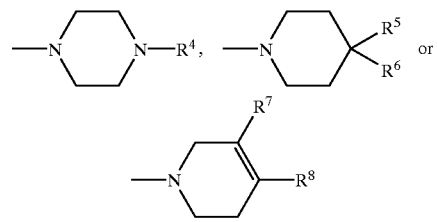

wherein
Y is hydrogen, hydroxy, cycloalkyl of 3 to 15 carbon atoms, or phenyl, phenoxy, naphthyl, naphthyloxy, heteroaryl, or heteroaryloxy, wherein the heteroaryl or the heteroaryl group of heteroaryloxy is selected from thienyl, furanyl, pyridinyl, indolyl, chromanyl, coumarinyl, carbostyrilyl, and quinolinyl;

R[3] is hydrogen or alkyl of 1 to 6 carbon atoms;

n is an integer from 0 to 6;

R[4] is hydrogen, alkyl of 1 to 6 carbon atoms, phenyl, ω-phenylalkyl, co-diphenylalkyl, wherein the alkyl chain contains 1 to 4 carbon atoms, indolyl, indazolyl, pyridinyl, pyrimidinyl, quinolinyl, benzoisothiazolyl, or benzisoxazolyl;

R[5] is hydrogen, hydroxy, cyano or carboxamido;

R[6] is hydrogen, 1-benzimidazol-2-onyl, benzoisothiazolyl, or benzisoxazolyl, or —Q—Ar;

Q is C=O, CHOH, or $(CH_2)_m$, m is an integer from 0 to 4;

Ar is phenyl; or

R[5] and R[6], taken together with the carbon atom to which they are attached, form

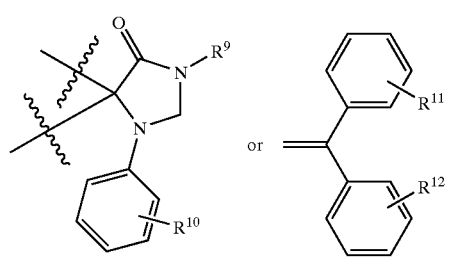

R[7] is hydrogen;

R[8] is phenyl, naphthyl, thienyl, benzoisothiazolyl, or benzisoxazolyl;

R[7] and R[8], taken together with the carbon atoms to which they are attached, form a benzene ring;

R[9] is hydrogen or alkyl of I to 6 carbon atoms; and

R[10], R[11] and R[12] are, independently hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or a pharmaceutically acceptable salt thereof;

wherein said phenyl, phenoxy, naphthyl, naphthyloxy, heteroaryloxy. ω-phenylalkyl, ω-diphenylalkyl, indolyl, indazolyl, pyridinyl, pyrimidinyl, quinolinyl, benzoisothiazolyl, benzisoxazolyl, 1-benzimidazol-2-onyl, or thienyl groups, or the benzene ring, are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms. or alkanesulfonamido of 1 to 6 carbon atoms.

34. A method of claim 33 wherein the subject is a human.

35. A pharmaceutical composition comprising a therapeutically effective amount of a compound of formula I:

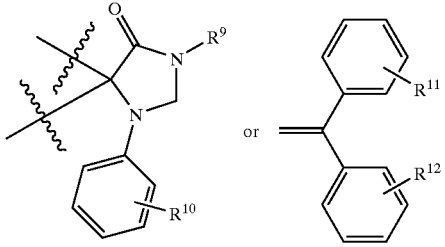

wherein $R^1$ and $R^2$ are, independently, hydrogen, halo, cyano, carboxamido, carboalkoxy of two to six carbon atoms, trifluoromethyl, alkyl of 1 to 6 carbon atoms, alkoxy of I to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

Z is $NR^3\text{-}(CH_2)_n\text{—}Y$,

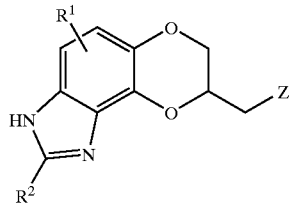

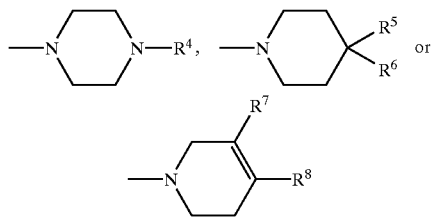

wherein

Y is hydrogen, hydroxy, cycloalkyl of 3 to 15 carbon atoms, or phenyl, phenoxy, naphthyl, naphthyloxy, heteroaryl, or heteroaryloxy, wherein the heteroaryl or the heteroaryl group of heteroaryloxy is selected from thienyl, furanyl, pyridinyl, indolyl, chromanyl, coumarinyl, carbostyrilyl, and quinolinyl;

$R^3$ is hydrogen or alkyl of 1 to 6 carbon atoms; is an integer from 0 to 6;

$R^4$ is hydrogen, alkyl of 1 to 6 carbon atoms, phenyl, co-phenylalkyl, ω-diphenylalkyl, wherein the alkyl chain contains 1 to 4 carbon atoms, indolyl, indazolyl, pyridinyl, pyrimidinyl, quinolinyl, benzoisothiazolyl, or benzisoxazolyl;

$R^5$ is hydrogen, hydroxy, cyano or carboxamido;

$R^6$ is hydrogen, 1-benzimidazol-2-onyl, benzoisothiazolyl, or benzisoxazolyl, or —Q—Ar;

Q is C=O, CHOH, or $(CH_2)m$, m is an integer from 0 to 4;

Ar is phenyl; or $R^5$ and $R^6$, taken together with the carbon atom to which they are attached, form $R^8$ is phenyl, naphthyl, thienyl, benzoisothiazolyl, or benzisoxazolyl, $R^7$ and $R^8$, taken together with the carbon atoms to which they are attached, form a benzene ring;

$R^9$ is hydrogen or alkyl of 1 to 6 carbon atoms; and $R^{10}$, $R^{11}$ and $R^{12}$ are, independently hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms; or a pharmaceutically acceptable salt thereof; wherein said phenyl, phenoxy, naphthyl, naphthyloxy, heteroaryloxy, ω-phenylalkyl, ω-diphenylalkyl, indolyl, indazolyl, pyridinyl, pyrimidinyl, quinolinyl, benzoisothiazolyl, benzisoxazolyl, 1-benzimidazol-2-onyl, or thienyl groups, or the benzene ring, are optionally substituted with substituents selected from hydrogen. halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms, and a pharmaceutically acceptable carrier or excipient.

36. A compound of claim 1 wherein at least one of said phenyl, phenoxy, naphthyl, naphthyloxy, heteroaryloxy, ω-phenylalkyl, ω-diphenylalkyl, indolyl, indazolyl, pyridinyl, pyrimidinyl, quinolinyl, benzoisothiazolyl, benzisoxazolyl, 1-benzimidazol-2-onyl, or thienyl groups, or the benzene ring, bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

37. A compound of claim 33 wherein at least one of said phenyl, phenoxy, naphthyl, naphthyloxy, heteroaryloxy, ω-phenylalkyl, ω-diphenylalkyl, indolyl, indazolyl, pyridinyl, pyrimidinyl, quinolinyl, benzoisothiazolyl, benzisoxazolyl, 1-benzimidazol-2-onyl, or thienyl groups, or the benzene ring, bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

38. A compound of claim 35 wherein at least one of said phenyl, phenoxy, naphthyl, naphthyloxy, heteroaryloxy, ω-phenylalkyl, ω-diphenylalkyl, indolyl, indazolyl, pyridinyl, pyrimidinyl, quinolinyl, benzoisothiazolyl, benzisoxazolyl, 1-benzimidazol-2-onyl, or thienyl groups, or the benzene ring, bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

* * * * *